US009659030B2

(12) United States Patent
Colaco et al.

(10) Patent No.: US 9,659,030 B2
(45) Date of Patent: May 23, 2017

(54) WEB SERVER FOR STORING LARGE FILES (71) Applicant: INTERNATIONAL MEDICAL SOLUTIONS, INC., Mississauga (CA)

(72) Inventors: Vernon Colaco, Mission Viejo, CA (US); Vittorio Accomazzi, Toronto (CA)

(73) Assignee: INTERNATIONAL MEDICAL SOLUTIONS, INC., Mississauga (CA)

( * ) Notice: Subject to any disclaimer, the term of this patent is extended or adjusted under 35 U.S.C. 154(b) by 508 days.

(21) Appl. No.: 14/082,115

(22) Filed: Nov. 16, 2013

(65) Prior Publication Data

US 2014/0115020 A1  Apr. 24, 2014

Related U.S. Application Data

(62) Division of application No. 13/541,719, filed on Jul. 4, 2012, now Pat. No. 9,298,730, and a division of application No. 13/692,916, filed on Dec. 3, 2012, now abandoned.

(51) Int. Cl.
| | | |
|---|---|---|
| *G06F 15/16* | (2006.01) | |
| *G06F 17/30* | (2006.01) | |
| *G06F 19/00* | (2011.01) | |

(52) U.S. Cl.
CPC ...... *G06F 17/30194* (2013.01); *G06F 19/321* (2013.01)

(58) Field of Classification Search
CPC .................. G06F 17/30194; G06F 19/321
See application file for complete search history.

(56) References Cited

U.S. PATENT DOCUMENTS

| | | |
|---|---|---|
| 6,182,127 B1 | 1/2001 | Cronin, III et al. |
| 6,658,462 B1 | 12/2003 | Dutta |
| 2002/0016718 A1 | 2/2002 | Rothschild et al. |
| (Continued) | | |

FOREIGN PATENT DOCUMENTS

EP        1217556 A2        6/2002

OTHER PUBLICATIONS

Lefebvre, International Search Report and Written Opinion of the Searching Authority, PCT/CA2013/001051, Dec. 17, 2013.
(Continued)

*Primary Examiner* — Tonia L Dollinger
*Assistant Examiner* — Dixon Dabipi
(74) *Attorney, Agent, or Firm* — Vito A. Canuso, III (57) ABSTRACT

A system and method for processing large image files using HTML 5 employed by Web Browsers for efficiently process multiple images from the same or different sets of images by one or more client-side users contemporaneously, where the system includes a file server for storing native, processed, or partially processed, image files and meta data associated with the image files, a Web Viewer Cache for dynamic storage of such files and meta data such, a plurality of dedicated Web Servers to perform some or all of the image processing functionality, and a load balancer server dedicated to interfacing with one or more Web Browsers from client-side computers to direct, distribute and manage image retrieval and processing by the dedicated Web Servers regardless of whether a pre-fetch image processing request or a real-time image processing request has been made by the client-side computer users.

10 Claims, 9 Drawing Sheets

(56) References Cited

U.S. PATENT DOCUMENTS

| | | |
|---|---|---|
| 2003/0217116 A1 | 11/2003 | Currans |
| 2005/0054921 A1 | 3/2005 | Katsman et al. |
| 2007/0124410 A1 | 5/2007 | Hofstetter |
| 2007/0226320 A1* | 9/2007 | Hager ............... G06F 17/30194 709/219 |
| 2008/0021740 A1* | 1/2008 | Beane ................. G06F 19/321 705/3 |
| 2009/0103789 A1 | 4/2009 | Danner |
| 2009/0112882 A1 | 4/2009 | Maresh |
| 2009/0132285 A1 | 5/2009 | Jakobovits |
| 2010/0010983 A1* | 1/2010 | Crucs .................. G06F 19/321 707/E17.005 |
| 2010/0011087 A1 | 1/2010 | Hofsetter et al. |
| 2010/0138446 A1 | 6/2010 | Canessa et al. |
| 2011/0093293 A1 | 4/2011 | G. N. et al. |
| 2011/0110568 A1 | 5/2011 | Vesper et al. |
| 2011/0153351 A1* | 6/2011 | Vesper .................. G06Q 10/10 705/2 |
| 2011/0238618 A1 | 9/2011 | Valdiserri et al. |
| 2012/0096524 A1 | 4/2012 | Kavalan |
| 2012/0099769 A1 | 4/2012 | Eichhorn |
| 2012/0221354 A1* | 8/2012 | Wall .................... G06F 19/321 705/3 |
| 2012/0250956 A1 | 10/2012 | Bocirnea |
| 2012/0250990 A1* | 10/2012 | Bocirnea ............. G06T 3/4015 382/166 |
| 2012/0323606 A1 | 12/2012 | Ananthasubramanian et al. |
| 2013/0091026 A1 | 4/2013 | Deng et al. |
| 2013/0166767 A1* | 6/2013 | Olivier .................. H04L 65/60 709/231 |
| 2013/0305138 A1 | 11/2013 | Gicovate |
| 2013/0325493 A1 | 12/2013 | Wong et al. |
| 2014/0140589 A1 | 5/2014 | Klotzer |
| 2014/0143298 A1* | 5/2014 | Klotzer ............... H04L 67/2823 709/203 |
| 2014/0143299 A1 | 5/2014 | Klotzer |
| 2014/0143651 A1 | 5/2014 | Klotzer |

OTHER PUBLICATIONS

Lu et al (Oct. 2010): Research and Implementation of Converting DICOM Multi-Frame Medical Image to Multimedia Formal. 2010 International Conference on Multimedia Tech-zologyp. pp. 1-5.

Desai et al (Apr. 2011): Medical image transcoder for telemedicine based on wireless communication devices. 3rd International Conference on Electronics Computer Technology. pp. 389-393.

Liu et al (Apr. 2007): Medical Image Conversion with DICOM. Canadian Conference on Electrical and Computer Engineering. pp. 36-39.

Teng (Aug. 2009): Managing DICOM image metadata with desktop operating systems native user interface. 22nd IEEE International Symposium on Computer-Based Medical Systems. pp. 1-5.

"Roentgen Works—100% Browser-based DICOM Viewer, It's a DICOM Viewer!" http://www.roentgenworks.com/WebWorks.html.

Varma, "Managing DICOM images: Tips and tricks for the radiologist," Indian Journal of Radiology and Imaging, (Jan.-Mar. 2012), vol. 22, No. 1, pp. 4-13.

* cited by examiner

WEB SERVER FOR STORING LARGE FILES

RELATED APPLICATIONS

This application claims priority to patent application U.S. Ser. No. 13/541,719, filed on Jul. 4, 2012 by the inventors hereto, and U.S. Ser. No. 13/692,916, filed on Dec. 3, 2012 by the inventors hereto, the entire contents of which applications are incorporated herein by reference.

BACKGROUND

The embodiments herein relate generally to an improved Web Server for facilitating the storage and retrieval of large medical images using HTML 5 technology in general, and in particular an inventive Web Server Cache design configured to implement the facilitating functionality, and to balance the load among a plurality of Web Servers when more than one is used.

By way of background, certain terms are used herein that are worth defining for the benefit of the reader. In that regard, a Web server can refer to either the hardware (the computer) or the software (the computer application) that helps to deliver web content that can be accessed through the Internet. The most common use of web servers is to host websites, but there are other uses such as gaming, data storage or running enterprise applications. The primary function of a web server is to retrieve web pages requested by clients using Hypertext Transfer Protocol (HTTP). This means delivery of HTML documents and any additional content that may be included by a document, such as images, style sheets and scripts.

A user agent, commonly a Web Browser or web crawler, initiates communication by making a request for a specific resource using HTTP and the server responds with the content of that resource or an error message if unable to do so. The resource is typically a real file on the server's secondary storage, but this is not necessarily the case and depends on how the Web Server is implemented. While the primary function is to serve content, a full implementation of HTTP also includes ways of receiving content from clients. This feature is used for submitting web forms, including the uploading of files and, in the case of embodiments of the present invention, asynchronous JavaScript and XML (AJAX) request (see, e.g., http://en.wikipedia.org/wiki/Ajax_(programming)).

Many generic Web Servers also support server-side scripting using Active Server Pages (ASP), PHP, or other scripting languages. This means that the behavior of the Web Server can be scripted in separate files, while the actual server software remains unchanged. Usually, this function is used to create HTML documents dynamically as opposed to returning static documents. The former is primarily used for retrieving and/or modifying information from databases. The latter is typically much faster and more easily cached.

Web Servers are not always used for serving the World Wide Web. They can also be found embedded in devices such as printers, routers, webcams and serving only a local network. The Web Server may then be used as a part of a system for monitoring and/or administering the device in question. This usually means that no additional software has to be installed on the client computer, since only a Web Browser is required.

A Web Browser is a software application for retrieving, presenting and traversing information resources on the World Wide Web. An information resource is identified by a Uniform Resource Identifier (URL) and may be a web page, image, video or other piece of content. Hyperlinks present in resources enable users easily to navigate their browsers to related resources. Although browsers are primarily intended to use the World Wide Web, they can also be used to access information provided by Web Servers in private networks or files in file systems. Examples of Web Browsers include Google Chrome™, Mozilla Firefox™, Internet Explorer™, Opera™, and Safari™.

HTML 5 is a markup language used for structuring and presenting content for the World Wide Web and is a core technology of the Internet. It is the fifth revision of the HTML standard (created in 1990 and standardized as HTML 4 as of 1997). Its core aims have been to improve the language with support for the latest multimedia while keeping it easily readable by humans and consistently understood by computers and devices (web browsers, parsers, etc.). HTML 5 is intended to subsume not only HTML 4, but also XHTML 1 and DOM Level 2 HTML.

Following its immediate predecessors HTML 4.01 and XHTML 1.1, HTML5 is a response to the fact that the HTML and XHTML in common use on the World Wide Web are a mixture of features introduced by various specifications, along with those introduced by software products such as web browsers, those established by common practice, and the many syntax errors in existing web documents. It is also an attempt to define a single markup language that can be written in either HTML or XHTML syntax. It includes detailed processing models to encourage more interoperable implementations; it extends, improves and rationalizes the markup available for documents, and introduces markup and application programming interfaces (APIs) for complex web applications. As explained below, this feature is employed in embodiments of the present invention as described in detail below because the HTML is used as front end of the web application that is written in JavaScript and runs within the browser. The HTML page retrieved by the browser therefore contains:

a. JavaScript code that implements the application's logic and based on user input dynamically retrieve information from the web server using AJAX request and update the interface.

b. The HTML 5 that defines the application's interface (button, text, layout and so forth). The content of the application interface is changed dynamically by the JavaScript that invokes the HTML 5 APIs, as well as creates and/or destroys HTML 5 objects Turning back to background information, traditionally load balancing is a computer networking method for distributing workloads across multiple computing resources, such as computers, a computer cluster, network links, central processing units or disk drives. Load balancing aims to optimize resource use, maximize throughput, minimize response time, and avoid overload of any one of the resources. Using multiple components with load balancing instead of a single component may increase reliability through redundancy. Load balancing is usually provided by dedicated software or hardware, such as a multilayer switch or a Domain Name System server Process.

Digital Imaging and Communications in Medicine (DICOM) is a standard for handling, storing, printing, and transmitting information in medical imaging. It includes a file format definition and a network communications protocol. DICOM enables the integration of scanners, servers, workstations, printers, and network hardware from multiple manufacturers into a picture archiving and communication system (PACS). The different devices come with DICOM conformance statements that identify which DICOM classes they support. DICOM has been widely adopted by hospitals and is making inroads in smaller applications like dentists' and doctors' offices.

Figure 1A:
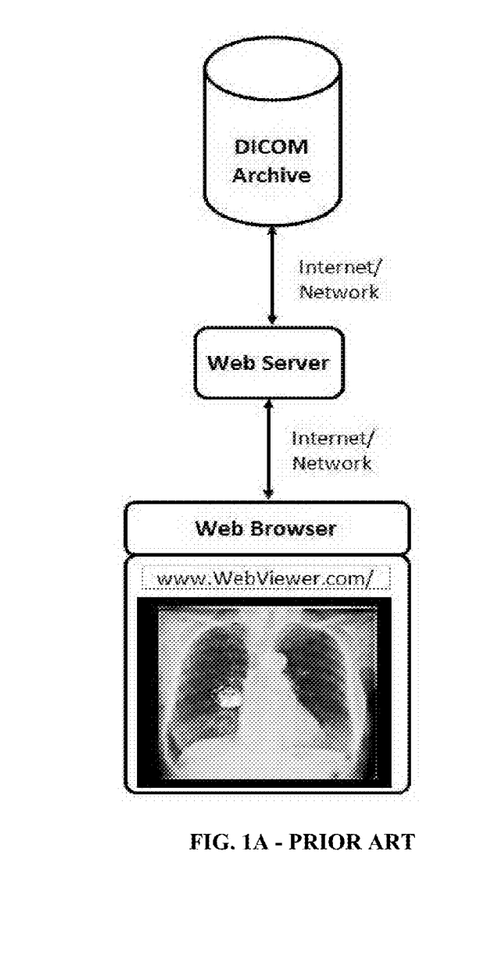
FIGS. 1A and 1B show schematic view and flow chart of the operation of prior art systems, often referred to as server-side rendering.
Figure 1B:
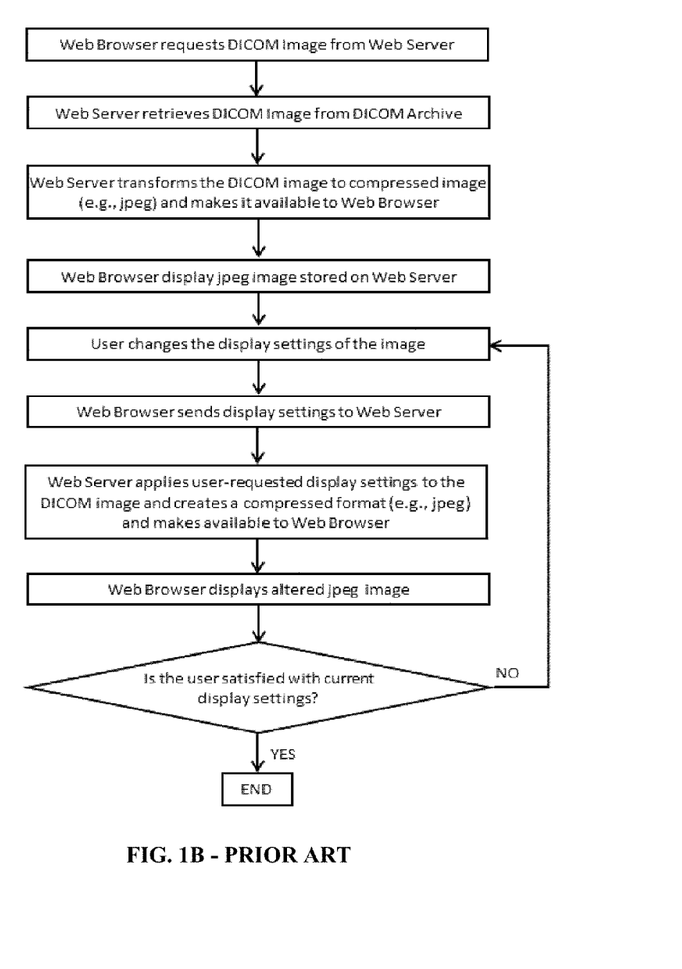

In hospital settings, it is very common to view medical images provided on a Web Server that functions, among others, to archive and process digital images (i.e., an image archive) using a Web Browser to view the images. The medical images are most often in DICOM formatting, which are typically very large size files. Referring to FIGS. 1A and 1B, DICOM images (or other formatted files) are stored on a DICOM archive 1 (or an archive or other formatter files), which is connected via a DICOM network, or other Internet or network pathway 2, to a dedicated Web Server 3, which then processes the images for transmission to a computer 4 using a Web Browser 5 employing HTML to a viewer, such as a computer monitor 6. In some cases, the images are stored on a remote website accessible by the clinician through the computer or on local memory associated with the clinician's computer.

DICOM images store a value which is up to 16 bits per each pixel (and therefore from 0 to 65536), while jpeg images only 8 bit (and therefore from 0 to 256). This is important because normal computer monitors can often only display 256 values. Therefore, when a DICOM image is displayed, the system must determine how to map the 16 bits values from 0 to 65536 into 256 values. This operation is called "window level" and is done very frequently to medical images. It visually allows changing the brightness and contrast of the image. The window level is typically set by the doctor in order to see specific anatomy on the image. While viewing medical images, clinicians often change the display parameters (such as brightness, contrast, and zoom). Other operations include panning the image to visualize the most relevant part, and/or measuring the image.

Given the size of conventional DICOM image files, a conventional Web Browser is unable to retrieve and transmit the DICOM image. The HTML 4 standard allows a web page only to display an image that resides on the Web Server. This is accomplished with the "img" tag. Under this restriction the Web Server has to perform all the image operations such as pan, zoom and window level. Thus, many hospital computer systems employing HTML 4 language rely upon server-side rendering, which slows down the process.

Referring to FIG. 1B, an example of server-side rendering includes the manipulation of a DICOM image into a compressed image (e.g., jpeg) using the dedicated Web Server. The user's (or hospital system's) Web Browser, which is capable of transmitting jpeg images, can then be used to retrieve the image, whereby the client may then enhance the image by varying its quality and/or effects. With this infrastructure, the Web Server functions as a rendering engine that produces images more easily accessed and transmitted by the Web Browser. As such, the Web Browser is not directly accessing the image file in the Web Server's cache, but rather the "rendered" version of the original image file as processed by the dedicated Web Server. A typical transaction may proceed as follows: the Web Browser requests to view an image; the image is transferred from the DICOM archive to the Web Server; the image is converted to jpeg (or equivalent) and made available to the Web Browser; the Web Browser requests that certain operations (rendering) be applied to the images; the Web Server applies the requested operations, and the Web Server makes the transformed images (e.g., converted jpeg images) available to the Web browser 6, which can then be used by the user to view the images.

The new HTML 5 standard permits a web page to generate and display images without having to request them from the Web Server. This is accomplished with the "canvas" tag. Embodiments of the invention, as explained further below, take advantage of this, and other features so that the Web Browser, and more specifically the JavaScript code included in the web page, can be used to retrieve the 16-bit data of the image to display from the Web Server and display the image applying the display parameters set by the user (window level, pan and zoom) locally. The display-dependent operations are done locally with the Web Browser without requiring any processing from the dedicated Web Server.

SUMMARY

Embodiments of image processing systems are provided that are configured to process large image files while enabling the features of HTML 5 employed by one or more Web Browsers within the image processing system, where the systems are preferably configured to efficiently process multiple images from the same or different sets of images by one or more client-side users contemporaneously by distributing the processing work load between a plurality of web servers each configured to perform a part or all of the image processing functionality. In some embodiments, the image processing system comprises a file server configured to store native, processed, or partially processed, image files and meta data associated with the image files, the file server comprising a Web Viewer Cache, the Web Viewer Cache configured for dynamic storage of such files and meta data such that the files and meta data dynamically stored are limited to those that are most used and/or most likely to be used in the near future; a plurality of dedicated Web Servers configured to perform some or all of the image processing functionality as assigned to the Web Servers depending upon their availability and processing capability, the Web Servers comprising a pre-fetch image processor and a real-time image processor, the former configured to retrieve and process images for storage on the Web Viewer Cache for later access by a client-side user, the latter configured to retrieve and process images for storage on the Web Viewer Cache for real-time access by a client-side user; and a load balancer server dedicated to interfacing with one or more Web Browsers from client-side computers to direct, distribute and manage image retrieval and processing by the dedicated Web Servers regardless of whether a pre-fetch image processing request or a real-time image processing request has been made by the client-side computer users, wherein the image processing system is configured to interface with a dedicated image archive stored on a separate server and/or dedicated memory and with a plurality of client-side computer users, where each of the plurality of computers comprises a Web Browser employing HTML 5 capability.

BRIEF DESCRIPTION OF THE FIGURES

The detailed description of some embodiments of the invention will be made below with reference to the accompanying figures, wherein like numerals represent corresponding parts of the figures.

DETAILED DESCRIPTION OF CERTAIN EMBODIMENTS

Embodiments of the present invention comprise a combination of Web Servers, a Load Balancer Server, a Web Viewer Cache Server, and a Web Browser accessible from one or more computers. The Web Browser, and thereby the embodiments, take advantage of some of the features of HTML 5, and provide for more efficient medical imaging viewing. The Web Browser contemplated for use with the inventive embodiments is functionally capable of rendering the images with the new 'canvas' tag introduced in HTML 5 images, so the role of the Web Server changes from a server-side rendering machine to a data processor that pre-processes the data and stores the results in the Web Cache; i.e., converts the medical images into a format that can be transmitted using HTTP. At a high level, the processing comprises parsing the DICOM file such that the information can be easily retrieved by the JavaScript in the HTML page using AJAX, for example. In one case, the Web Server may extract the pixel data of the image (as 16 bits), extract the DICOM tags from the image, and save them in JSON such that they can be quickly accessed by the Web Browser web page. In other cases, the Web Server may also create auxiliary files, such as thumbnails, of the images, On the client end, the user may vary the display parameters, which can now be handled by the Web Browser, rather than the servers in the prior art.

Some embodiments of the present invention include a pre-fetch feature, taking advantage of the independence of the imaging processing from the display adjustments. With such a feature, one or more Web Servers are configured to pre-process ahead of time images that are likely to be requested in the near future, rather than in real time. Of course, the Web Servers are configured to process the images in real time as well; i.e., when a user requests certain images for access at the time of the request. Thus, some embodiments of the present invention comprise both real time processing and pre-fetch processing by the Web Servers. In that regard, a Load Balancer Server is preferably provided in some embodiments to distributed and manage the work load performed by the one or more Web Servers to optimize processing, particularly in situations where there are numerous client-side users seeking access to DICOM images within the same or different study.

Figure 2A:
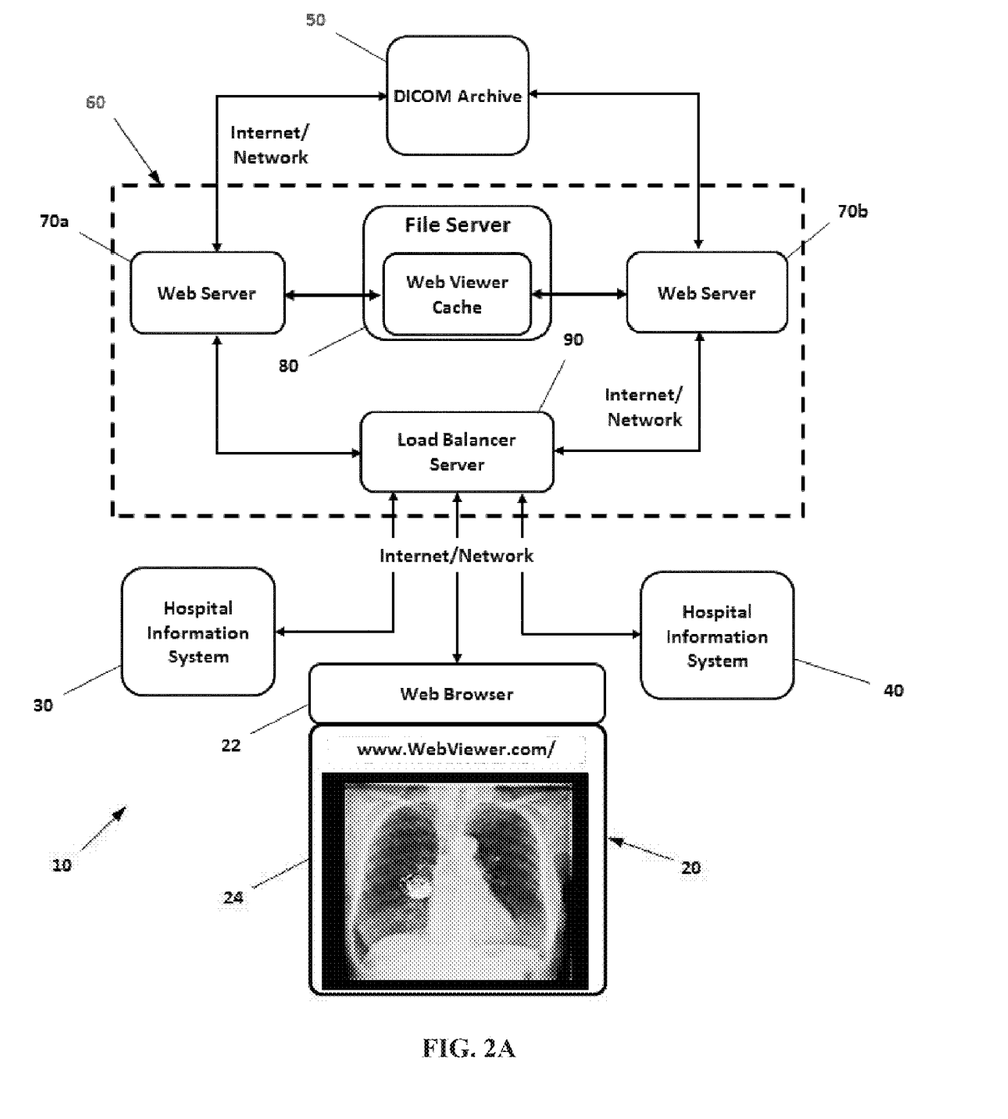
FIGS. 2A and 2B show a schematic view and corresponding flow chart of the system and operation of one embodiment of the present invention, functioning as a client-side rendering system, where one or more dedicated Web Servers are employed along with a Load Balancer Server and one or more Web Browsers employing HTML 5 functionality to efficiently process one or more studies that include DICOM images requested by clinicians in the hospital environment.
Figure 2B:
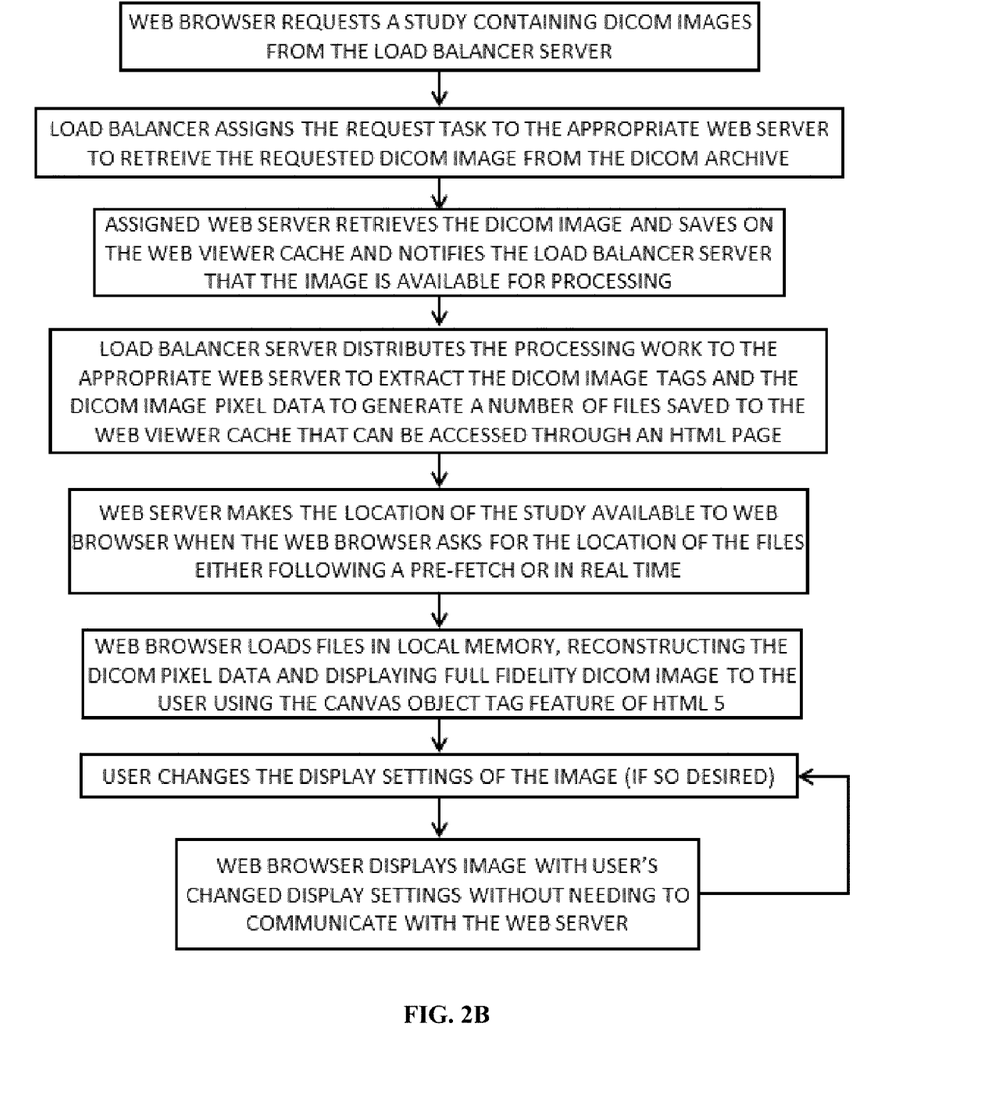

Referring to FIG. 2A, in one example embodiment, a client-side system 10 comprises one or more computers 20 comprising Web Browsers 22 employing HTML 5 software and a monitor 24 for viewing the images. The client side system 10 also may include a Hospital Information System (HIS) 30 and/or a Radiology Information System (RIS) 40, and a DICOM Archive 50, where the computers 20 are within or without the HIS 30 or RIS 40. In other words, the location of the viewing computer may be anywhere within the client-side system, and the computers may be configured such that some are used for image processing requests and some are used for image viewing and display manipulation. It should be noted that embodiments of the present invention may be applicable to other types of images other than DICOM images; thus, DICOM images are referred to herein by example only.

Through the use of computers 20 within or without the HIS 30 or RIS 40, requests for and access to DICOM images may be made through the use of system components 60. In some embodiments 10, the system components 60 comprise one or more Web Servers 70a, 70b, a Web Viewer Cache Server 80, which may be simply a file server on which Viewer Cache capabilities are programmed, and a Load Balancer Server 90 if so desired. Connections between the individual components of the system components 60, and the connections between the computers 20 within or without the HIS 30 and RIS 40 are made via one or more of numerous possible interfaces, such as a private network, a public network, and/or the Internet. The connection vehicle is not critical to functionality of embodiments of the present invention.

When an image is desired to be accessed, the client (which may be the HIS or RIS as described below) opens up the Web Browser notifies the server of which images are desired to be viewed in the next few hours. Embodiments of the pre-fetch feature have at least two benefits: one, they reduce the peak usage of the server and, therefore, the capital cost (as the server would be otherwise sized based upon the peak usage demanded) and, two, they improve the response time to the system as the user will find the images already in the server's Web Cache and, thus, does not have to wait for the server to receive the images from the DICOM archive and then parse them. This may be referred to as client-side rendering, and improves display frame rate and quality of image without compression. The Web Server is now doing much less work, because it is no longer doing rendering, but just permitting access by storing it. More details about the Web Server Cache are provided below.

In that regard, embodiments of the invention beneficially optimize the design of the Web Server Cache structure for the data processing role of the Web Server. The Web Browsers load the data directly from the Web Server Cache and display them to the user locally. So the design is more efficient, because the Web Server is not involved functionally for user display. With some embodiments, the Web Server Cache is configured to synchronize amongst multiple servers to maintain consistency of the data over time. This includes a load balancing capability, to most efficiently process data. Importantly, the improved Web Servers are configured to be accessed by multiple Web Browsers simultaneously, even when multiple servers are being employed in synchronous operation. The Web Server Cache is also configured to detect the failure of any server being employed in data processing, and restart the processing steps handled by the failed server using another server.

Figure 6A:
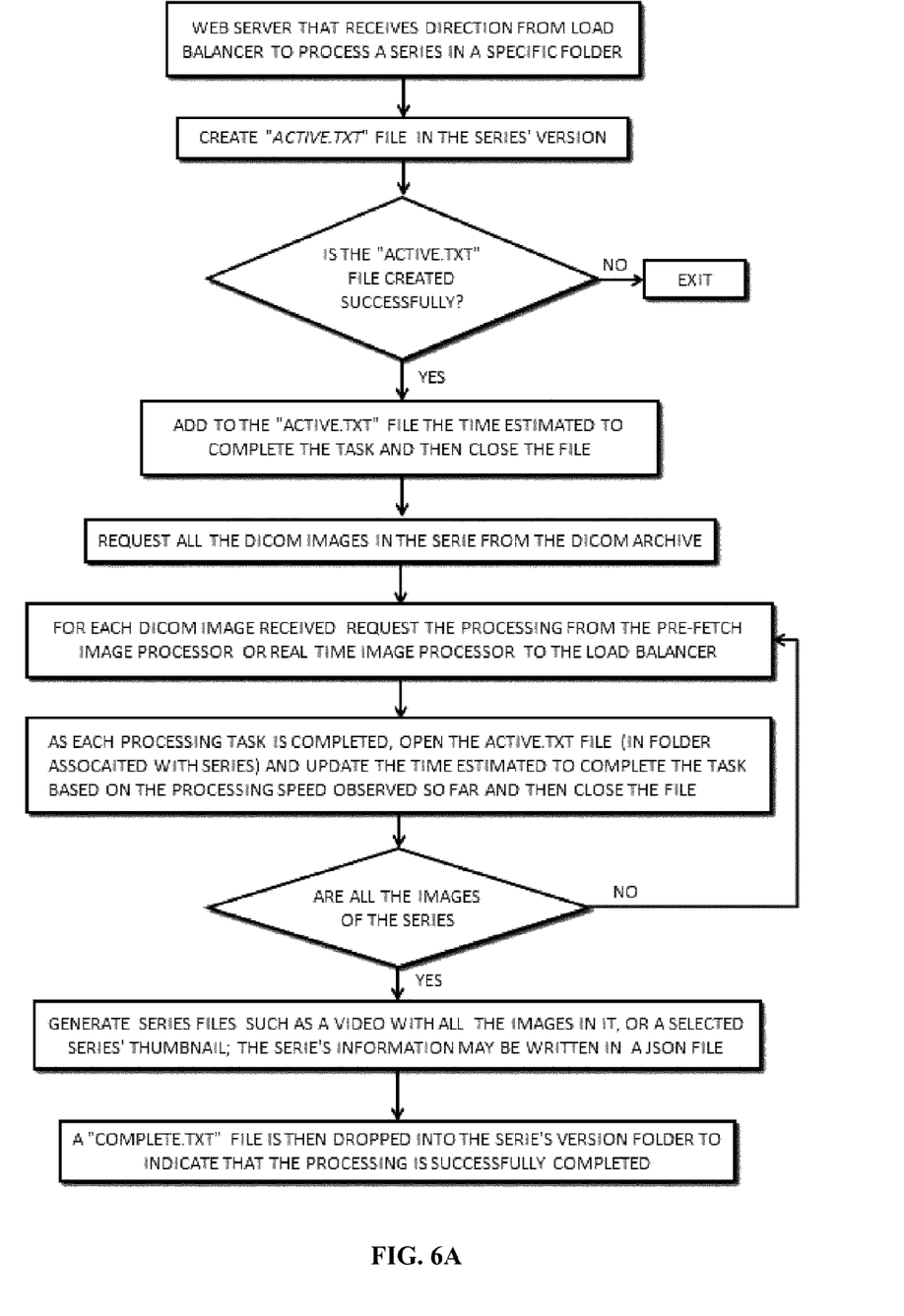
FIGS. 6A and 6B show flow charts with greater detail of operation of embodiments of the present invention.
Figure 6B:
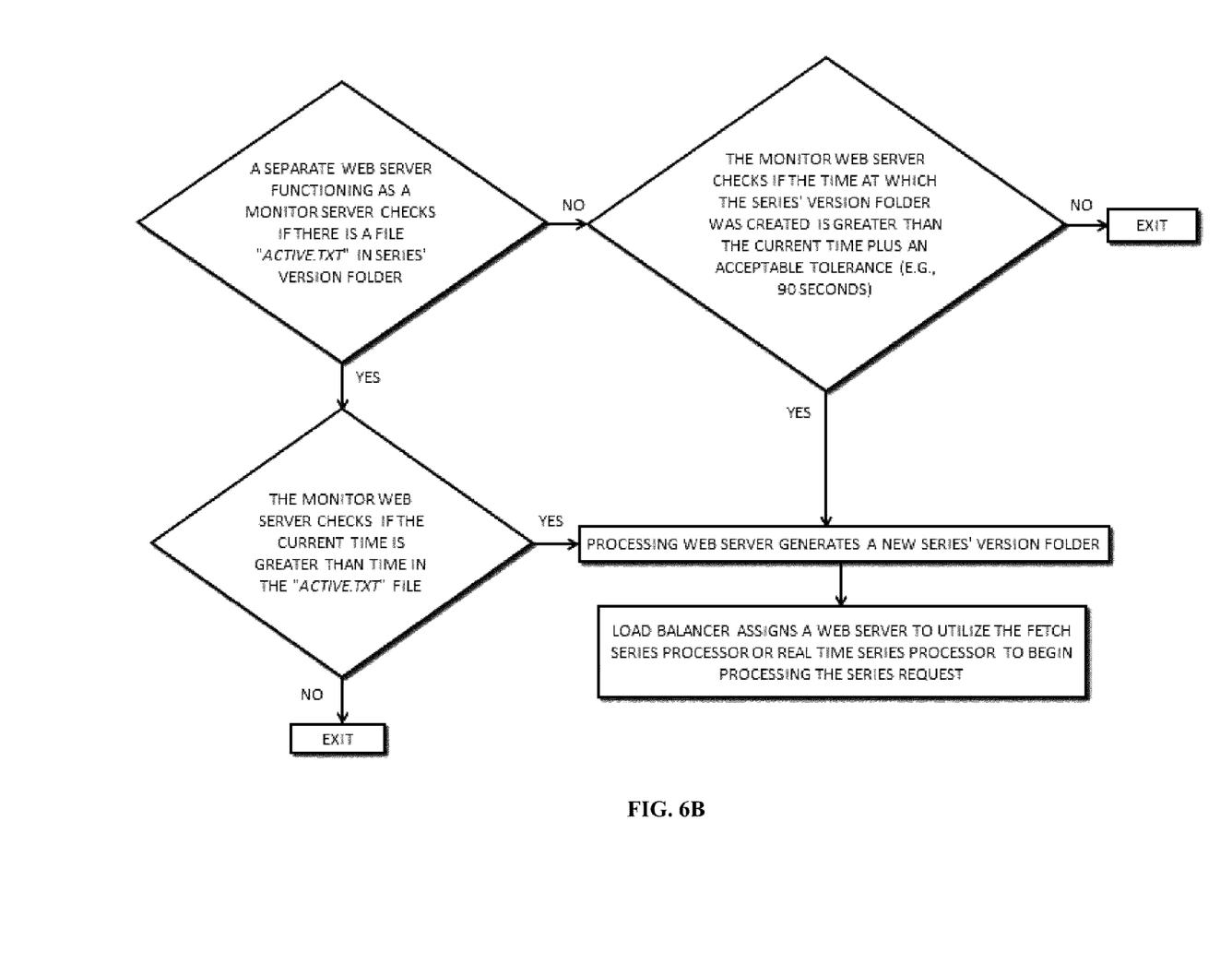

In some embodiments of the present invention, the system is configured to optimize load balancing among multiple servers, with the ability to maximize the system responsiveness to user requests. In one example embodiment, load balancing is achieved by structuring the processing of the medical images such that it is split equally across all the servers. With the present invention, load balancers may be provided that are programmed and tailored specifically to automatically handle particular system applications utilizing a plurality of Web Servers, such as large hospital settings. As may be appreciated from some of the functionality described below, it is contemplated that load balancers of some embodiments be configured to prevent two different Web Servers from performing the same functionality when contemporaneous requests are made for the same study. In other cases, the same functionality may be assigned by a less sophisticated load balancer, but then internal functionality, such as is described in association with FIG. 6B below, may be employed. Indeed, in some cases, off-the-shelf load balancers may be employed with embodiments of the system. In certain embodiments, multiple load balancers may be employed where the size of the application (i.e., number of users sharing one or more large image archives) is sufficiently large to dedicate certain groups of Web Servers to certain functionalities, as may be described herein by example.

As explained above, embodiments of the inventive Web Server are configured to permit a clinician to make a data access request, where patient information, image information, and/or image location may be provided. The data access request is preferably generated by a Web Browser on the clinician's computer. The Web Server then preferably performs the appropriate processing necessary to satisfy a data access request while the clinician awaits the results of the query. In some embodiments, pre-fetch data processing may be requested, as described for example by the inventors in U.S. patent application Ser. No. 13/692,916, filed on Dec. 3, 2012 hereto, the entire contents of which application are incorporated herein by reference. In preferable system embodiments, both pre-fetch and real-time data requests are permissible, with the embodiments being configured to permit one or more users to make pre-fetch requests of some studies while other users may make real-time requests of the same or different studies. The order of availability where overlap in requests occurs would be handled by the load balancer in combination with the plurality of Web Servers based upon a priority and/or chronology of requests. Where updates are made to the studies, embodiments of the system are configured to ensure that the latest version of the study is being made available to the servers, and that only one server is updating the study at a time. It is contemplated that, in some embodiments, contemporaneous requests of the same study may trigger copies of the study to be made temporarily for dual visibility where no changes to the study may be permitted (so as to avoid creating inadvertent errors in later access to the most up-to-date version of the study). It is contemplated that reconciliation functionality may be employed so that dual visibility and changes may be made where the dual-revised studies may be joined automatically to create a further updated version incorporating both sets of changes to the extent they can be reconciled. The point is that additional functionality may be employed by tailoring the system as desired for certain applications. Thus, some embodiments are configured to permit such tailoring of the system as desired or needed.

Often in large hospital there are hundreds of users viewing medical images requiring the use of numerous Web Servers. With multiple requests be made by either the same clinician, or by multiple clinicians using multiple Web Browsers, embodiments of the inventive Web Server are configured to distribute the requests across all the available server using the load balancer feature. In some cases, the real time processing and the pre-fetch data processing requests are split in two steps such as the processing of the single images is distributed across the servers. This may be provided, in some embodiments, by employing a common disk Web Cache for the images which is shared across all the Web Servers, which are all connecting to a medical imaging archive. An example of the creation of a Web Server is with Windows™ Server 2008 R2, Microsoft IIS™, and/or equivalent. The load balancer may be a discrete component from the Web Server functionality, or may be incorporated within the Web Servers or the Web Server Cache.

Figure 3:
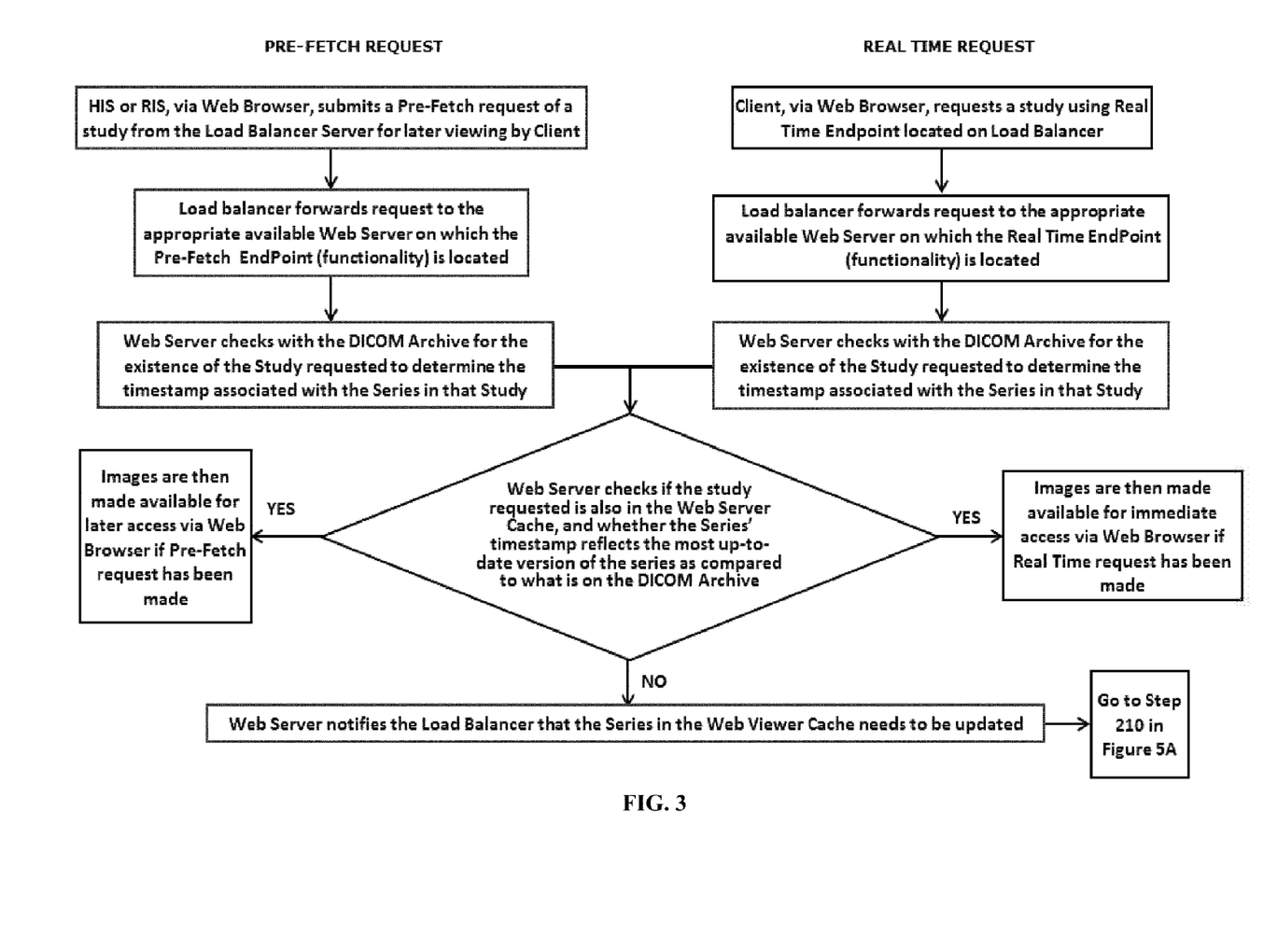
FIG. 3 shows a flow chart of operation of Pre-Fetch and Real Time requests as implemented by embodiments of the present invention, including the embodiments depicted in FIGS. 2A and 2B.

Referring to FIG. 3, one embodiment of the load balancing feature may be described in more detail. In that regard, both pre-fetch and real-time requests can be made and processed as reflected in the flow chart. In both cases, the load balancer is configured, in this example, to forward the request to the appropriate available Web Server on which the Pre-Fetch EndPoint (functionality) is located. In certain embodiments, the requests in each group will be managed as a queue based upon first in and first out (FIFO). The requests in each one of the groups above will be mapped into Web Server end points, such that work can be distributed automatically across the server using the load balancer; priority of each one group can be easily configured at the server level. Toward this end, tools such as Microsoft® IIS provides basic infrastructures, such as "Application Pool," that allows control of the resource used by a Web Application and so by a set of end points.

Figure 4:
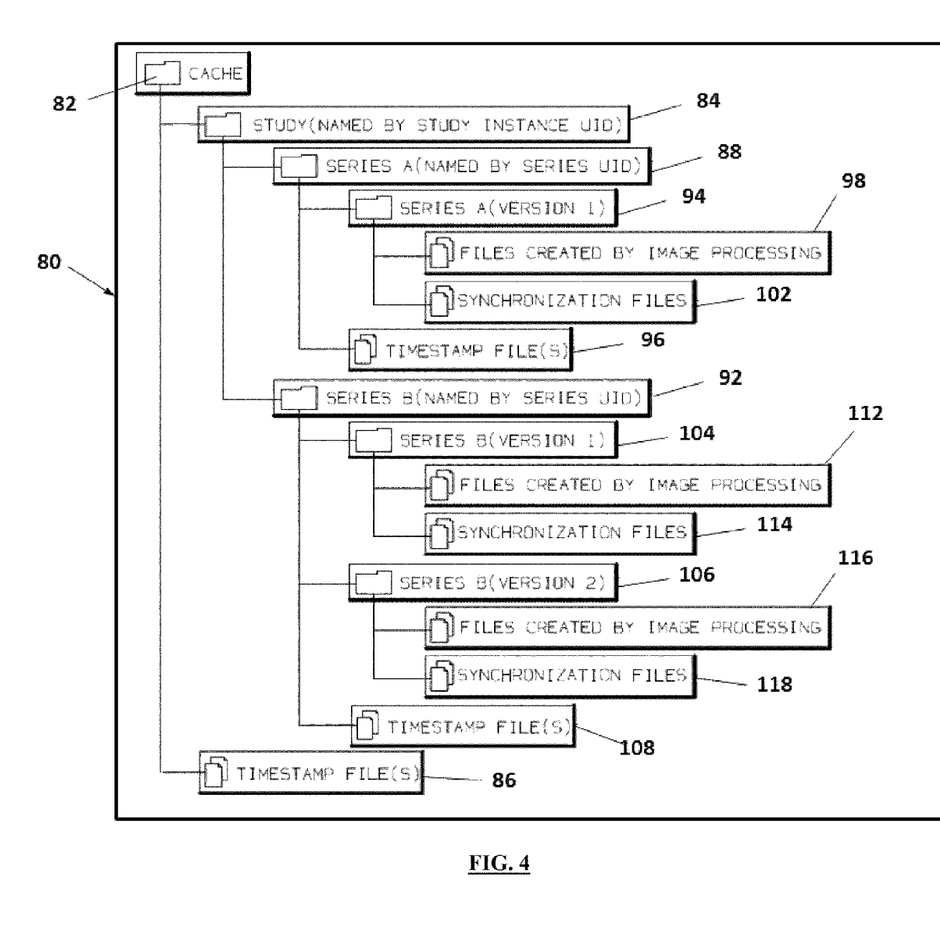
FIG. 4 shows an example of the contents of a study stored on the one embodiment of the Web Viewer Cache.
Figure 5A:
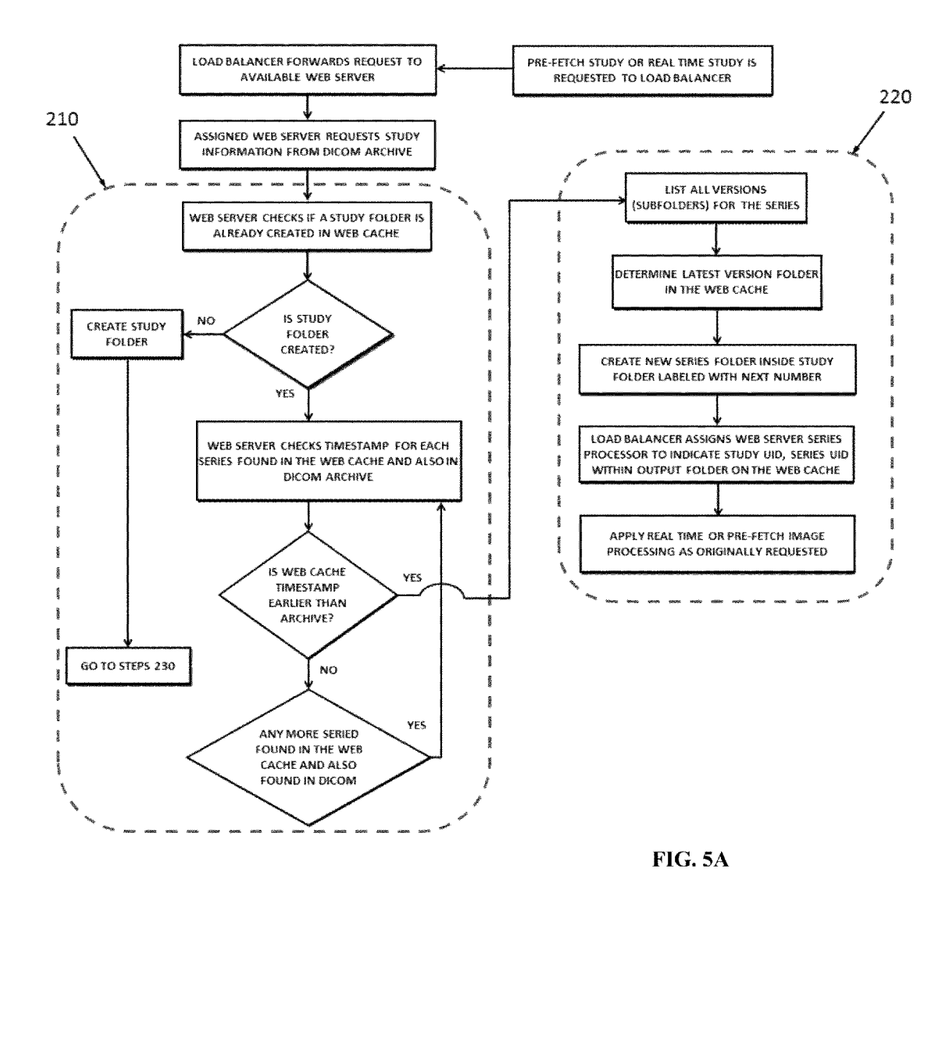
FIGS. 5A and 5B show a single flow chart containing four series of examples of steps employed in embodiments of the present invention, with greater detail of operation provided.
Figure 5B:
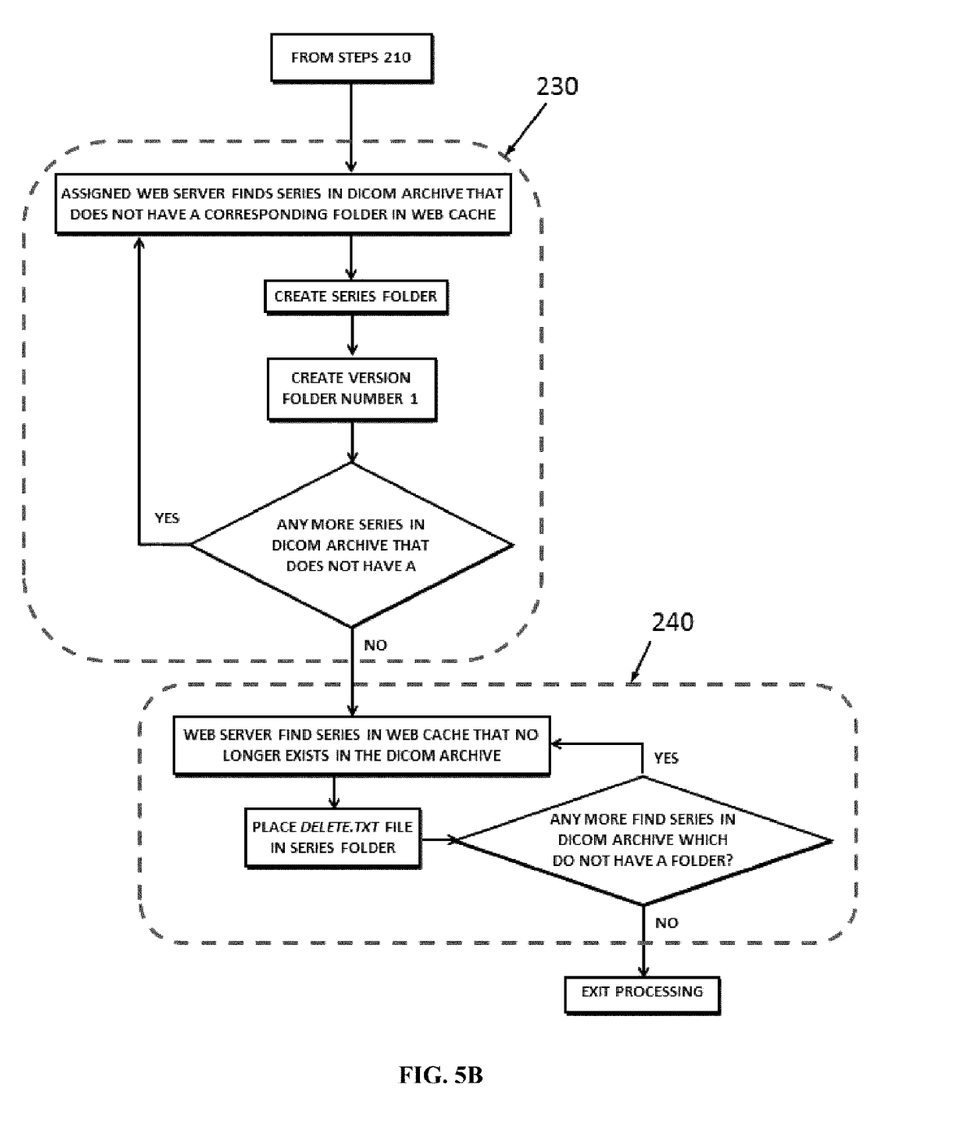

Referring to FIG. 4, one example of the structure of the Web Cache may be appreciated. Preferably unique IDs are used to identify the study and the series within the study. Under each series folder there are timestamp files that indicate the time at which the version assigned with the highest number is created. Using these files the Web Server upon a request for a study can check if the time stamp for each series in such a study is the most recent as indicated by the DICOM archive; or start the processing if it is not. Once the processing of a series is complete, the series processor drops a "complete.txt" file in the series revision folder. Once a Web Server receives a data access request for a study it will provide to the Web Browser the link to the files on the folder with the highest number. The Web Server will mark the study as complete if all the highest version of the series are marked as completed (the ones that contain the "complete.txt" file). When a series has been deleted, the Web Server will drop a file called "delete.txt" on the series' folder in order to indicate to the data access function that the series does not have to be returned to the Web Server queries any more.

It is worth noting that the time stamp is a value that indicates when the last changes to a series or study has been made. It can be an ordinal number (for instance the number of ticks—see http://en.wikipedia.org/wiki/System_time) or the actual date and time. The time stamp of a series, therefore, preferably reflects either that the an image was added, removed or replaced, and/or when the image was added, removed or replaced. Similarly, the time stamp of a study reflects if the last series was modified, when the last series was modified (an image was added, removed or replaced), and/or whether a series was added or removed and/or when. A DICOM archive may be configured to keep track of the time stamp of the series and studies within the archive, but presently there is no provision in DICOM for the communication of such value. Thus, the time stamp can be determined by the Web server implementing a DICOM extension or implementing a non-DICOM communication with the archive all together. Alternatively the series time stamp can be implemented using a combination of Series Acquisition Dates and also number of images in the series by the Web Server. Similarly the time stamp of a Study can be implemented as the latest time stamp of all the series and the number of them. A variety of possible arrangements and formats are contemplated with embodiments of the present invention.

In one example of a Web Cache 82 within Web Cache Server 80, a study 84 may be stored comprising time stamp files 86 including time stamp associated with the study. Studies may have multiple series depending upon whether subsets of images are desired or appropriate. For example Series A 88 and Series B 92 may exist, each of which have versions reflective of earlier and later updates and/or modifications. Series A 88 may comprise Version 1 94, with time stamp files 96, where the Version 1 94 itself comprises files 98 created by the image processing functionality, as well as synchronization files 102. The same may be true for Series B 92, which may comprise one or more versions 104, 106, each similarly comprising processed image files 112, 116 and synchronization files 114, 118, all by example.

Referring to FIGS. 5A, 5B, 6A and 6B, operation of embodiments of the system may be described in more details. For purposes of reference, steps 210 comprise a situation where a study exists in the DICOM (or large image) archive as well as the Web Server Cache, where the Cache version is up to date and ready for access. Steps 220 comprise a situation where a study exists in the DICOM (or large image) archive as well as the Web Server Cache, but the Cache version is out-of-date relative to the archive. Steps 230 comprise a situation where a study exists in the archive, but no version of it exists on the Cache. Steps 240 comprise a situation where a study exists in the Cache, but is no longer on the archive. In such cases, the Cache version may be deleted.

Using the architecture as described by example herein, when a Web Server receives a data access request, it will check if the study requested is present in the Web Cache; if not it will preferably issue a real time processing request that can be sent to the load balancer, which will forward it to the first server available. The server will start the processing as described below. When a Hospital Information System (HIS) or Radiology Information System (RIS) issues a pre-fetch request the server will check if the study requested is in the Web Cache. If not, it will issue a pre-fetch data processing request to process the study. For the purpose of this example, the data access request can be considered being generated by the Web Browser for the intent to retrieve study information and images to display to the viewer. So for the purpose of this example, one request in this group may be referred to as the "Study Request". Client data processing requests are issued by the Web Server upon a data access request for a study that is not present in the Web Cache or for which the Web Cache does not contains the most recent version. There are two types of real time processing requests: series processing and image processing, which are described below. Similarly, pre-fetch requests are issued by an external agent (typically HIS or RIS) to the Web Server. The Web Server will preferably check if the study requested is in the Web Cache and if the copy is up to date. If not it will issue a pre-fetch data request. As with real time processing, there are two pre-fetch data processing functions: series processing and image processing.

Once the Web Browser issues a data access request for a study not present in the Web Cache, the Web Server creates a study folder, to inform other servers that the processing is taking place, and then issues a series processing request for each series in the study. The pre-fetch data processing request include a "pre-fetch" request which is issue by the HIS or RIS to inform the Web Server that a study will be requested in few hours. Upon the processing of this request the server will check if the study is in the Web Cache and, if not, it creates a study folder and then it issues a "series processing request," which is included in this group and is not part of the "real time processing" group. In turn the "series processing request" will issue a number of "image processing request" which again are part of the pre-fetch data processing group rather than the real time processing. Both the "real time processing" and "pre-fetch data processing" provide "series processing request" and "image processing request", which perform the same operation, however it is important to keep them separate because the priority in which the request are processed depends on the group which they are in. Because data processing requests in general can be very time-consuming to process, it is extremely important that the series and images processing request issued by a data access (and therefore in the group "real time processing") to be processed with much higher priority than series and images processing request issued by the pre-fetch, because the former have a user in front of the Web Browser waiting for the data to be displayed, and the latter don't have a user waiting for it. As mentioned above the data processing tasks can heavily vary in processing time due to the study size.

In order to deal properly with this and spread the work across multiple servers the data processing (either client requested or pre-fetch) are implemented as Web Server End Points as follow: series processing, which comprises a. transferring the series from the archive to the Web Cache, which is common to all the Web Server's instances, b. updating the timestamp in the series folder, c. issuing an image processing request for each image being transferred providing the location of the DICOM image file and output files, and d. generating series information and possibly post-processing of the images in the series once all the images processed have been completed, and marking the processing of the series as completed. With regard to image processing, that comprises in some example, a. processing the input image (extracting meta information, pixel data and so forth), b. storing the output of the processing in the image Web Cache, and c. removing the input image if necessary.

It is important to note that the granularity of the processing is at the image level, this decision is determined by the number of images can vary tremendously in each series, and therefore if the work is not spread across several servers it might happen that servers are idle while other servers are not able to process the entire request. Given that the entire set of servers share the same Web Cache, they all can access the same set of images without incurring extra transfer cost. Furthermore the cost of invoking a Web Server End point is quite minimal, and so spreading the processing across several servers doesn't increase the processing time. The load balancer policies are preferably fairly simplistic, such as round robin, although may be as complex as desired by the user and the provider of the system. In other terms the load balancer, when distributing the work for an End Point across several servers, does not check if the server is busy or not. So the fact that it is distributing the work at the lowest granular level (image) helps ensure the optimal load balancing is occurring. It is to be noted that in some embodiments, it is preferable to have a single Web Cache that can be accessed by all the Web Servers, as this prevents servers from processing multiple times the same study. This also allows the server that runs the series processor to store the images in a location that is accessible to every server and therefore request the processing of the images to a different server. It has to be noted that transferring a series from the DICOM archive is more efficient that transferring a single image. Therefore, the fact that the Web Cache is shared across all the servers allows the system to take advantage of this optimization.

The Web Cache would necessarily have a maximum size, and once it exceeds that capacity, a clean up process would preferably automatically analyze all the data in the Web Cache and remove some of it. At any Data Access request the Web Brower receives the list of DICOM images processed and available on the Web Cache. The Web Server indicates to the Web Browser if the processing is completed or not. In the case in which is not the Web Browser will typically re-request the study information in few seconds until it receives the indication that it is completed.

For each DICOM image the browser will receive a link to the following: a file with meta information on the DICOM image; i.e., information stored in the DICOM tags in, for example, JSON format, an image at different resolutions of the DICOM image in jpeg format, used as a preview, and files that store the 16-bit pixel data of the DICOM image. In one embodiment, the file is stored as raw 12-bit values, which then enables IIS compression (see e.g., http://technet.microsoft.com/en-us/library/cc771003(v=ws.10)aspx) to compress the file dynamically when sending them to the browser. Other methods of storing the files in an HTML compatible format are described in the patent application incorporated by reference herein.

Once the browser receives a list of the files above will access them as requested by the user. The browser accesses the files above directly bypassing the Web Server (but not IIS) in order to minimize the cost on the web server. Therefore once the Web Browser receives the list of file which represent an image, it is completely independent from the server and it can access them at any time. The communication between the browser and the server in this regard is completely ended.

Embodiments of the inventive Web Server Cache overcome challenges that such a Web Cache would otherwise face. First is Web Cache integrity; because all the Web Servers can read and write data in the Web Cache, there must be a synchronization mechanism to guarantee Web Cache integrity. For instance it must guarantee that once the same study is requested to multiple servers only one initiates the processing procedure outlined above. The second is fault tolerance; a server might not be able to complete its task because of hardware or network failure. The inventive embodiments account for that, and direct another server to take over and complete the processing task. The third is uncontrolled client access; the Web Server may not monitor the access to the Web Cache from the Web Browser. Once the browser receives the list of files in the Web Cache it can access them at any time. Thus, embodiments of the invention are configured such that different versions of the same study or series can be access at the same time by different browsers, and the server is configured to remove files from the Web Cache periodically.

As different versions of the same study can be viewed at the same time by different clients, the Web Server is configured to assign a version to the link of the images provided to the client. In some embodiments, the actual series are assigned a version, not the entire study. This is preferably in situations were often only few series are changed (added, removed or modified) in a study. The series is element that is assigned a version in the Web Cache and updated. For this reason the data processor provides the function to process an entire series.

Web Servers can be synchronized in a number of ways, including using databases. In some embodiments of the inventive Web Servers, one efficient way to synchronize is to use the file system. This relies on the fact that a file-create operation is atomic; i.e., if multiple Web Servers try to create the same file at the same time, only one will succeed and all the other will fail. Only the successful Web Server may continue the processing, while the others may just wait for its completion. So in the case in which the same study is being requested via multiple servers at the same time, they will all create the study folder, the series folder and version folder. This does not present a problem because the creation of a folder that already exists is not deemed an application error. So all the servers will preferably launch a series processor pointing to the same series folder and version folder. The first operation of the series processor is to create a file called "active.txt" in the destination folder. When a file is created by the Web Server, only the server that created that file is the server that can process the series until it is complete. If the assigned Server goes down, the system can detect that a "complete.txt" file does not exist, so a different server will be assigned to restart the processing from scratch. In other words, given that the file creation is an atomic operation, only one series processor will succeed and the other will fail. Only the series processor that succeeds will continue the processing and the other will stop the computation. Using this example of a scheme helps ensure that only one server will process the data in a folder at any given time.

At any time only one Web Server might be requesting data from a specific series from the archive, and generate a corresponding distributing-image-processing task for it. This Web Server is the one responsible to save the series-related information, such as the timestamp and the "complete" flag. The server might also perform post-processing across all the images of the series, for instance to select a series thumbnail or generate a video with the series' images.

After being launched, the series processor is monitored by the data access because the Web Browser will preferably keep checking for when the study's data is completed. Once the series processor starts the processing, it will create a file called "active.txt" where it writes the time at which it is expected to complete the task. The file will be updated as the data is being received from the archive because the number of images and the speed at which the servers are able to process them may not be known up front. If the Web Server—upon a data access request—finds a series in which "complete.txt" is not present, it will check the time of the expected completion in "archive.txt." If the time has passed, it will be assumed that the processing task has died. Thus, in some embodiments, it will create a new version folder and it will launch a new series processor for such series. Such an approach is fault tolerant at several levels: if the series processor is just under-estimating the completion time, the system will process twice the same series, yet it will work properly because the processors are working on different version's folders; if a Web Browser has a link to the data on the version folder which is not completed, the link is still valid. In the rare case in which the series processor even fails to create the "active.txt" file the data access will check the creation time of the folder and only if a significant time has passed will it attempt to create a new series' version folder. As the fault detection relies on the data access polling information until the study transfer is completed, it will be postponed in case of pre-fetch. In such case the fault will be detected when the user tries to access the study. Alternatively the server itself could auto-generate data access request for such study.

With regard to Web Cache eviction, for an HTML 5 viewer the Web Cache is preferably configured to store all the data being viewed by the Web Browsers connected. For optimal performance, it should be sized in order to keep the data generated by the Web Server for a fairly large time, for instance 24 hours. In one example, assume that the Web Cache is set to hold the result for at least H hours. At regular intervals, at each instance that the Web Server starts a process, it will check the Web Cache's size, and in the event in which the size is greater then a fixed threshold it will try to remove some of the study. In order to determine which studies to remove the process will examine the "last access time" attribute for each file in each study folder, and it will then sort all the studies based on the most recent access time found. It then will start considering removing the studies for which the most access time found is at least H hours passed. In the occasional case in which a Web Browser has been open on the same study for more then a pre-designated number of hours (i.e., a time limit), the JavaScript code in it will preferably automatically access a single file in the study, possibly disregarding the content. This will cause the "last access time" of such file to be updated in the Server's Web Cache, and therefore the study will not be evicted by the Web Cache. Notice that using the 'last access time' is just one possible implementation. This feature is sometimes disabled in Windows® NTFS file systems for performances reasons. An alternative way to implement the methodology above is to have the data access create an empty file (called lastaccess.txt) on the study folder once the Web Browser requests the content information. The Web Cache eviction process would preferably identify the last time the study was accessed by just checking the creation time of the lastaccess.txt file. This approach has some advantages because it does not rely upon the file system settings and is more efficient because the Web Cache eviction process does not have to access all the files in the study folder but just once. If the file lastaccess.txt is not present in the folder, that situation signifies that the study has been pre-fetched but not viewed yet by the Web Browser, and so it should be left untouched. However there is also a possibility that a study which was pre-fetch was not accessed. Therefore, it is preferably that the Web Cache eviction process check the creation time of the study folder to determine if it has to be evicted.

Thus, embodiments of the present invention provide several benefits. The system is able to have several viewers accessing different version of the same study. The Web Cache is configured to keep track of the files being accessed so when the Web Cache storage level exceeds those set by the user (or the manufacturer of the memory), the Web Server Cache can identify which files are least used or have not been recently used and can remove them from Web Cache memory without affecting Web Browser operation. Applying a timestamp to the files permits the Web Server to determine whether the data in the Web Cache is the most updated version; i.e., if the processing had to be restarted or whether further processing of the data occurred later or on a different server. The system is fault tolerant, and under any condition it keeps the integrity of the file provided to the Web Browser. The systems help ensure that the viewer is always able to access the files needed in the Web Cache, and the study being viewed will not be evicted.

In one application of an embodiment of the invention, the Web Server is configured and programmed to function as follows:
  a. for each medical study, a folder is create named with a study-unique identifier;
  b. for each series in the study, a subfolder is created named with a series-unique identifier;
  c. for each version of the series, a subfolder is create named with the series number;
  d. in each series-version folder, the processed files are stored, the synchronization files (i.e., active.txt and complete.txt) are stored, and the timestamp for the series; and
  e. for each folder stored on a server that is detected to be failing, a new series version is created.

Once the Web Browser requests a study from the Web Server, some applications of embodiments of the invention will proceed as follows:
  w. the Web Server requests the study information from the DICOM archive that contains the series list and a time stamp associated with each one of them.
  x. the Web Server checks if the study folder is created. If not it will try to create it. If the creation fails it will be ignored.
  y. for each series folder in the study folder it will compare the time stamp with the time stamp returned by the archive. If they are different it will try to create a folder with higher version number inside the series folder. Then it will invoke the series processor for this series on this version folder; and
  z. for each series in the list returned by the archive, but without a folder in the study folder, it will create a folder and a subfolder with version 1. Then it will invoke the series processor on such series.

The Series Processor receives a unique identifier for the series to process and the destination folder (which includes the version). Possibly several Series processors may be launched at the same time for the same series and for the same destinations, as set forth in Steps "y" and "z" above. The first action of the series processor is to create a file called active.txt "as create new" in the destination folder. Only of the first series processor will be able to succeed in the creation of the file, this processor will be the one processing the series, the other ones will exit.

Of course it should be appreciated that embodiments of the present invention may be employed for all types of data and formatted files, not merely medical files or DICOM files specifically. Addition, the embodiments can be used for non-destructive testing. Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method of processing large image files stored in a central archive in a more efficient manner so that users can view such images remote from the archive, the image file processing method comprising:
  establishing a network comprising an accessible archived source of large image files, a file server comprising a web viewer cache configured to store output data associated with the large image files stored on the archived source of large image files, a plurality of web servers each configured to access and process the large image files stored on the accessible archived source for purposes of extracting output data associated with the large file images for storage on the web viewer cache, a load balancer server for balancing the processing load by the plurality of web servers, and at least one computer comprising a web browser configured to view the output data associated with a requested large image file; and configuring the web servers for (i) receiving a request from the web browser through the load balancer server to access related large image files, (ii) determining whether output data associated with the requested large image files is presently stored on the web viewer cache, (iii) if so, identifying to the web browser the location of the output data on the web viewer cache so that the web browser can access the output data for user viewing, (iv) if not, requesting of the load balancer that available web servers will be needed to process the requested large image files stored on the archived source so that associated output data can be stored on the web viewer cache, (v) the assigned web servers processing the requested large image files, (vi) extracting output data associated with a requested image files if assigned to do so by the load balancer server, (vii) storing the output data on the web viewer cache for identification to the web browser.

2. The method of claim 1, wherein the web servers are further configured so that when the web server receiving the request for a large image file finds associated output data stored on the web viewer cache, the web server verifies whether the output data in the web viewer cache reflects the most updated version of the requested related large image files stored on the archived source before identifying the location of the output data on the web viewer cache to the web browser.

3. The method of claim 2, wherein verifying comprises determining whether a time stamp associated with the output data file on the web viewer cache is later in time than a time stamp associated with the corresponding large image files on the archived source.

4. The method of claim 2, wherein the web servers are further configured so that when the web server determines that the requested large image files on the archived source of large image files reflect a later version of the corresponding output data stored on the web viewer cache, the assigned web server processing the later version of the large image files on the archived source of large image files and substituting the newly extracted output data in place of the older version of the output data on the web viewer cache so that the web browser can be notified of the location of the updated output data on the web viewer cache.

5. The method of claim 1, where a plurality of computers are incorporated within the network, each computer configured to permit a user to request certain large image files contemporaneously, and where the web servers are configured such that the contemporaneous requests can be processed by the web servers, as assigned by the load balancer server, contemporaneously.

6. The method of claim 1, wherein the web servers are further configured to process large image files in a pre-fetch mode of operation and in a real-time request mode of operation, the assigned web servers processing real-time requests before pre-fetch requests.

7. The method of claim 1, wherein processing a large image file comprises extracting meta data and pixel data as output data from the large image file and storing the output data on the web viewer cache for identification of the location of such output data to the web browser upon request.

8. The method of claim 7, wherein the output data further comprises a thumbnail image of the large image file.

9. A method of processing large image files stored in a central archive in a more efficient manner so that users can view such images remote from the archive, the image file processing method comprising:

establishing a network comprising an accessible archived source of large image files, a file server comprising a web viewer cache configured to store output data associated with the large image files stored on the archived source of large image files, a plurality of web servers each configured to access and process the large image files stored on the accessible archived source for purposes of extracting output data associated with the large file images for storage on the web viewer cache, and at least one computer comprising a web browser configured to view the output data associated with a requested large image file; and configuring the web servers for (i) receiving a request from the web browser to access related large image files, (ii) determining whether output data associated with the requested large image files is presently stored on the web viewer cache, (iii) if so, identifying to the web browser the location of the output data on the web viewer cache so that the web browser can access the output data for user viewing, (iv) if not, processing the requested large image files stored on the archived source to extract output data associated with a requested image files so that the output data can be stored on the web viewer cache, and (v) storing the output data on the web viewer cache for identification to the web browser.

10. The method of claim 9, wherein establishing a network further comprises a load balancer server for balancing the processing load by the plurality of web servers, and wherein configuring the web servers comprises (i) receiving a request from the web browser through the load balancer server to access related large image files, (ii) determining whether output data associated with the requested large image files is presently stored on the web viewer cache, (iii) if so, identifying to the web browser the location of the output data on the web viewer cache so that the web browser can access the output data for user viewing, (iv) if not, requesting of the load balancer that available web servers will be needed to process the requested large image files stored on the archived source so that associated output data can be stored on the web viewer cache, (v) the assigned web servers processing the requested large image files, (vi) extracting output data associated with a requested image files if assigned to do so by the load balancer server, (vii) storing the output data on the web viewer cache for identification to the web browser.

* * * * *